(12) United States Patent
Feleppa et al.

(10) Patent No.: US 8,292,812 B2
(45) Date of Patent: Oct. 23, 2012

(54) ULTRASONIC DETECTION OF BRACHYTHERAPY SEEDS BASED ON SINGULAR SPECTRUM ANALYSIS

(75) Inventors: Ernest J. Feleppa, Rye, NY (US); Jonathan Mamou, New York, NY (US)

(73) Assignee: Riverside Research Institute, New York, NY (US)

( * ) Notice: Subject to any disclaimer, the term of this patent is extended or adjusted under 35 U.S.C. 154(b) by 1280 days.

(21) Appl. No.: 12/004,670

(22) Filed: Dec. 21, 2007

(65) Prior Publication Data

US 2009/0163804 A1   Jun. 25, 2009

(51) Int. Cl.
*A61B 8/00* (2006.01)
(52) U.S. Cl. .................................................. 600/437
(58) Field of Classification Search .............. 600/407, 600/437, 439; 128/916
See application file for complete search history.

(56) References Cited

U.S. PATENT DOCUMENTS

| | | | |
|---|---|---|---|
| 6,238,342 B1 | 5/2001 | Feleppa et al. | |
| 6,447,438 B1 * | 9/2002 | Bernardi et al. | 600/3 |
| 6,490,472 B1 * | 12/2002 | Li et al. | 600/410 |
| 6,561,980 B1 * | 5/2003 | Gheng et al. | 600/443 |
| 7,217,242 B2 * | 5/2007 | Alam et al. | 600/439 |
| 2004/0039284 A1 * | 2/2004 | Alam et al. | 600/439 |

OTHER PUBLICATIONS

Mamou, J. et al., "Singular spectrum analysis applied to ultrasonic detection and imaging of brachytherapy seeds," J. Acoust. Soc. Am., 121(3), pp. 1790-1801 (Mar. 2007).
Mamou, J. et al., "Ultrasonic Imaging of Brachytherapy Seeds Based on Singular Spectrum Analysis," IEEE Ultrasonics Symposium, pp. 1107-1110 (Oct. 2006).
Pishchalnikov, Y.A., "Biomedical Ultrasound/Bioresponse to Vibration: Imaging, Wave Propagation, and Other Topics," J. Acoust. Soc. Am., vol. 119, No. 5, Pt. 2, pp. 3319-3321 (May 2006).

* cited by examiner

*Primary Examiner* — Brian Casler
*Assistant Examiner* — Nasir S Shahrestani
(74) *Attorney, Agent, or Firm* — Keith D. Nowak; Carter Ledyard & Milburn LLP

(57) ABSTRACT

The present invention provides a method for detecting and locating brachytherapy seeds using Singular Spectrum Analysis (SSA). The method exploits the presence of seed-specific repetitive echo signals in detecting seeds and determining their location. Radio frequency (rf) echo signals received from a scanned area of interest are converted to zero-mean envelope-detected signals and then processed using SSA to produce a spectral-power line (a P line). The P line indicates the relative likelihood of a seed being present. A colored P-mode image derived from a set of P lines is superimposed on a conventional ultrasound B-mode image to depict seed location.

7 Claims, 6 Drawing Sheets
(1 of 6 Drawing Sheet(s) Filed in Color)

ULTRASONIC DETECTION OF BRACHYTHERAPY SEEDS BASED ON SINGULAR SPECTRUM ANALYSIS

STATEMENT REGARDING FEDERALLY SPONSORED RESEARCH OR DEVELOPMENT

The present invention was made with funding support from National Institutes of Health Grant CA098465.

BACKGROUND OF THE INVENTION

The present invention relates generally to ultrasonic imaging and more particularly, to a method for detecting and imaging brachytherapy "seeds" using ultrasound signals.

Brachytherapy is a type of radiation therapy commonly used to provide local radiation for the treatment of localized cancers. One form of brachytherapy places multiple small cylindrical seeds of radioactive material inside or adjacent to a malignant tumor in order to emit radiation that can thwart the growth of cancer cells or kill them. Brachytherapy seeds are commonly used in treating gland-confined prostate cancer, but may also be used to treat brain cancers, breast cancers, and gynecological cancers. Seeds used in treating prostate cancers are generally small titanium-shelled radioactive seeds containing radioactive iodine ($I^{125}$) or palladium ($Pd^{103}$). The seeds are 4.5-mm to 5-mm long and 0.8 mm in diameter and consist of a thin, rigid, titanium shell enclosing the radioactive material.

Transrectal ultrasound (TRUS) is a standard imaging method frequently used to plan and guide implantation of brachytherapy seeds in the prostate. The TRUS probe is mounted on a fixture that contains a needle-guidance template, which rests against the perineum and incorporates detents enabling the probe to be introduced into or withdrawn from the rectum in 5-mm steps. Scans are oriented in a transverse plane perpendicular to the probe axis. The fixture is advanced into the rectum until the seminal vesicles are imaged and images of the prostate and adjacent tissues are generated.

TRUS images are ported through a standard output jack to a laptop computer on which treatment-planning software is run. An example of such software is VariSeed by Varian Medical Systems, Inc. (VMSI), of Charlottesville, Va. This treatment-planning software generates an image of available and optimal needle locations, which are fixed by the template used for needle guidance. The oncologist demarcates the prostate in each scan plane and prescribes a radiation dose for the gland as a whole. The planning software then presents a set of suggested seed positions in each scan plane, which the oncologist can accept or reject based on isodose distributions plotted by the software for whatever seed positions are chosen.

The software bases the isodose distributions on seed locations in the 3-D volume spanned by the set of scan planes in the planning set. Immediately after planning is completed, gland-immobilizing needles are inserted, and then seed-implantation needles are loaded with the radioactive seeds and plastic spacer seeds in a manner that places radioactivity at the specified depths, corresponding to the scan planes, along each needle position. The spacer seeds are not visible in ultrasonic or x-ray computed tomography (CT) images. Loaded needles are then inserted into the prostate via the perineum and through the template holes that match the needle positions depicted on the planning-software image. Dosimetric evaluation subsequently is performed using post-implant CT imaging. Traditionally, post-implant CT scans are performed within two to four weeks of implantation, but current practice tends to favor post-implant CT imaging within 24 hours of implantation.

Despite the use of gland-immobilizing needles, implantation using needles inserted transperitoneally causes gland movement and distortion, which often results in seed misplacement and dosimetry errors. In some cases, the CT scans show that the actual locations of implanted seeds differ markedly from their planned locations. Studies by Potters, et al., have shown that 30% of prostate brachytherapy procedures result in a dose to 90% of the prostate that is less than the prescribed dose. [Potters, et al., Int. J. Radiat. Oncol. Biol. Phys., 50:605 614, 2001]. Studies by Stock, et al., showed that 32% of under-dosed patients have biochemical failure (as evidenced by a rise in the blood level of prostate-specific antigen (PSA)) within four years, whereas only 8% of properly dosed patients have biochemical failure. [Stock, et al, Int. J. Radiat. Oncol. Biol. Phys., 41:101 108, 1998]. The conventional B-mode ultrasound images generated at the time of the procedure do not allow adequate visualization of the placed seeds because of clutter from calcifications and other hyperechogenic scattering objects, shadows caused by hemorrhage or by other seeds, and loss of echo signals due to seed angulation. Clutter often increases immediately during the procedure from hemorrhage and edema caused by the trauma of needle insertion. Other impairments in properly imaging seeds result from strong specular reflections of ultrasound waves reflected off the smooth titanium metal shell of brachytherapy seeds.

U.S. Pat. No. 7,217,242 describes an ultrasonic method for visualizing brachytherapy seeds. This patent is assigned to the same assignee as is the present application and the teachings of this patent are incorporated herein by reference. The invention described in the '242 patent is directed to a method for imaging therapeutic seeds in tissue by determining at least one mechanical resonant frequency for the seeds, stimulating the seeds with a first acoustic signal having a frequency corresponding to the resonant frequency and imaging the seeds with a second acoustic signal at a higher frequency. A Doppler method is used to detect vibratory motion and thus image the seeds. Although the method described in the '242 patent is a substantial advance over prior art methods for imaging therapeutic seeds, further advances are possible as described herein.

Currently, dosimetry corrections for seed misplacement are made after implantation and not intraoperatively. Accordingly, an imaging system is desired that can image seeds contemporaneous with seed implantation. A method is also desired that permits optimal seed placement and accurate dose distribution. An imaging system that provides accurate, post-insertion, seed-location information is also needed. Such real-time information would enable a physician to correct radiation dosage deficiencies intraoperatively in a patient by implanting additional seeds where needed. Finally, a method is desired to localize and image seeds and allow seed detection and depiction to be performed independently of transducer technology or beam-forming algorithms.

BRIEF SUMMARY OF THE INVENTION

The present invention relates to a method for ultrasonically imaging brachytherapy seeds using singular spectrum analysis (SSA). The method exploits the presence of seed-specific repetitive echo signals in detecting seed location. Specifically, envelope-detected, radio frequency (rf) echo signals received from a scanned area of interest are incorporated into the SSA to produce a P-line. P-line values indicate the relative likelihood of a seed being present. To visualize the seed location, a colored P-mode image derived from the P line is superimposed on a B-mode image to show seed location. The method of the present invention permits imaging brachytherapy seeds and thereby correcting dosimetry errors in the operating room during seed implantation.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention provides a method for detecting and locating brachytherapy seeds using singular spectrum analysis (SSA). The method exploits the presence of seed-specific repetitive echo signals in detecting seed location. SSA utilizes eigenvalues derived from the diagonalized correlation matrix of envelope-detected radio-frequency echo signals to yield a P value indicative of the likelihood of a seed-specific repetitive signal. The P value can be interpreted as a score for seed presence, which is combined with experimental observation that the first echo signal from a set of repetitive echo signals specifies the actual seed location.

In order to determine the characteristics of a brachytherapy seed when scanned with an ultrasound signal, a seed was inserted into an acoustically transparent gel standoff pad such as a 2 cm by 9 cm gel Aquaflex® pad made by Parker Laboratories of Fairfield, N.J. The pad was then scanned using a single-element, focused ultrasound imaging transducer such as the V326 5.0-MHz transducer manufactured by Panametrics, Inc. of Waltham, Mass. This particular transducer had an F number of 5 with a focal distance of 5 cm and an aperture of 1 cm. Three different single-element focused ultrasound transducers were used with nominal center frequencies of 3.5, 5.0 and 10.0 MHz, chosen to be in the range of 6 MHz generally used clinically to image the prostate.

Figure 1:
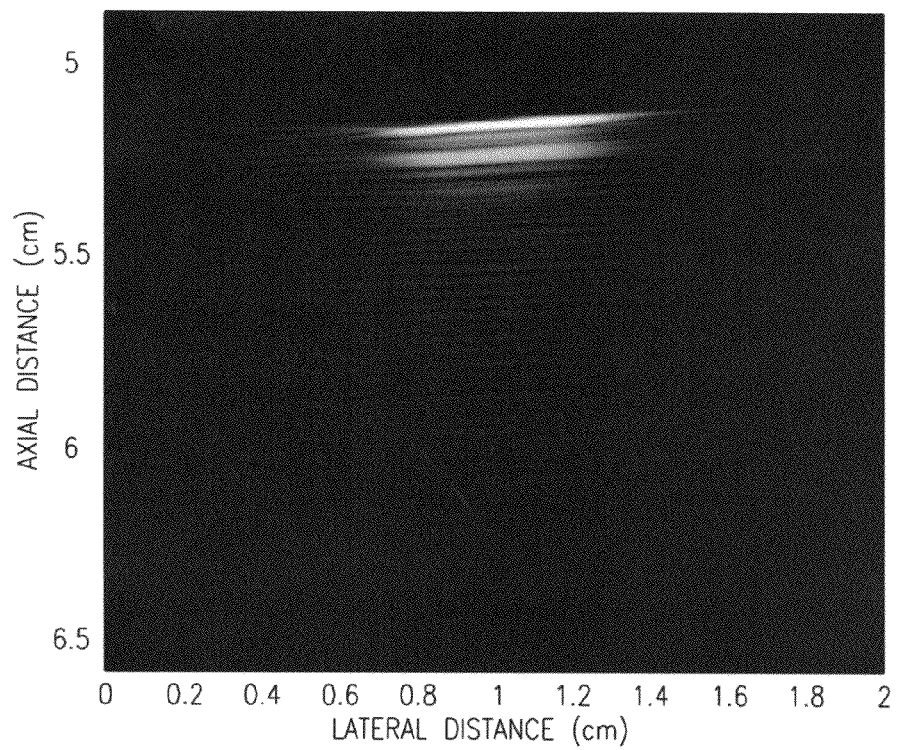
FIG. 1 illustrates a B-mode image of a seed in an acoustically transparent gel pad obtained with a 5.0 MHz center-frequency transducer.

The radio-frequency (rf) echo-signal data obtained by scanning the gel pad were digitized using a DP-110 A/D board, manufactured by Acqiris of Monroe, N.Y., which digitized 8-bit samples of the rf echo signals at a sampling rate of 50 MS/s. A desktop computer stored the digitized signals. FIG. 1 shows the B-mode image reconstructed from the rf echo-signal data. As shown in FIG. 1, the backscattered signals from the seed have a long "tail" of repeating echoes.

Figures 2A, 2B, 2C:
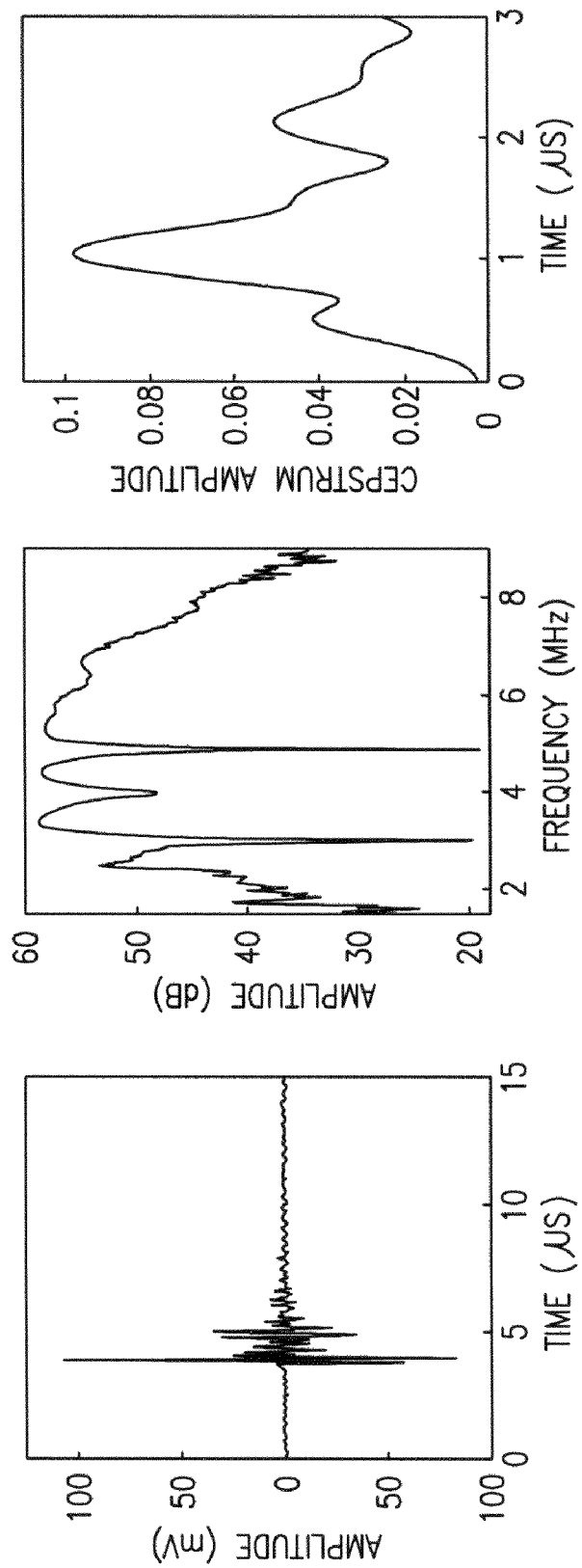
FIGS. 2A-2F show a backscattered rf signal and a log power spectra of the same signal.
Figure 2F:
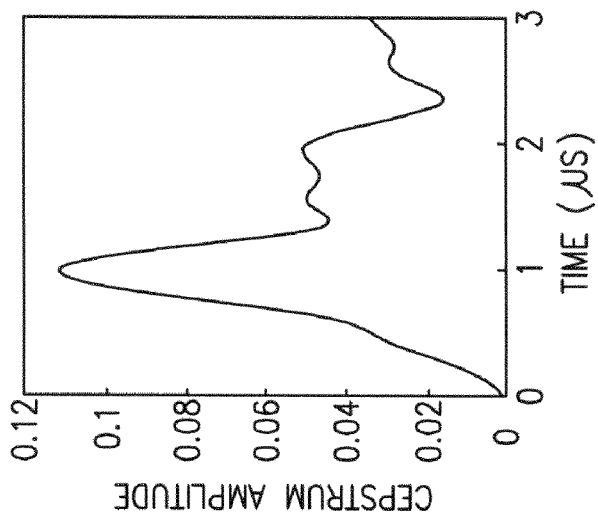
Figure 2E:
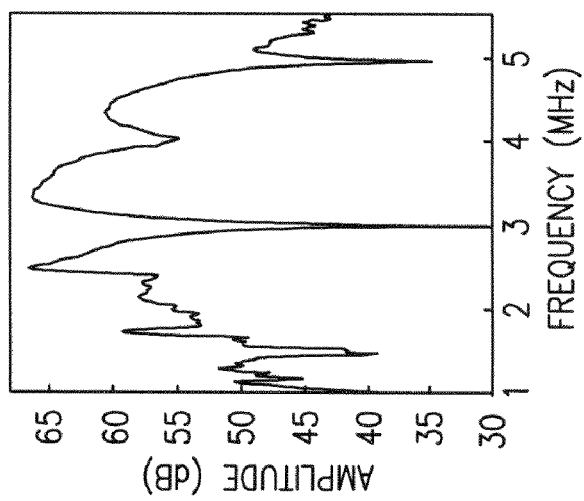
Figure 2D:
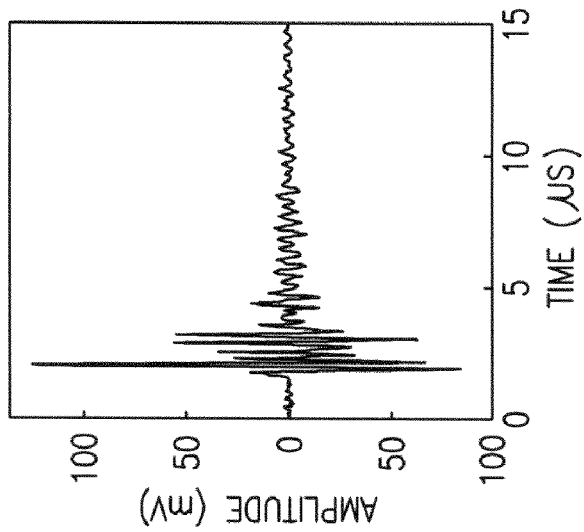

FIGS. 2A and 2D show a typical backscattered rf signal acquired with 5.0 and 3.5 MHz transducers showing two clearly visible echoes separated by approximately 1 µs. The first echo has a greater magnitude than the second echo and both are similar in shape. FIGS. 2B and 2E show the log power spectrum of the backscattered signal of FIGS. 2A and 2D and have periodic ripples about 1 MHz apart. The presence of scallops in the spectrum indicates repetitions in the corresponding time signal. FIGS. 2C and 2F show the computed cepstrum derived from the rf signals. (The cepstrum is the inverse Fourier transform of the log power spectrum.) Peaks in the cepstrum indicate repetitions in the time signals. The location of the cepstral peak in time denotes the period of the repetition. The single, clear peak near 1 µs indicates that the repetition period in the signal is approximately 1 µs. Consequently, the existence of a specific seed signature for the titanium-shelled, Pd, brachytherapy seeds is established by the above procedure consisting of a repetition frequency near 1 MHz. This finding is used in conjunction with the method of ultrasonic detection of brachytherapy seeds as set forth below.

In detecting and locating seeds, the present method utilizes the periodic nature of the seed signature described above in conjunction with a Singular Spectrum Analysis (SSA) to detect and then to display seed locations. A useful property of SSA is that periodic components (repetitions) generate eigenvalue pairs or, stated differently, eigenvalue pairs are synonymous with signal periodicity. SSA permits the detection of repetitions with very little sensitivity degradation from noise. The SSA framework is also beneficial in detecting repetitions because a heuristic criterion can be easily formulated to detect specific repetition periods. In the present invention, SSA is augmented with a method to retrieve localization information to detect and image seeds. More particularly, the SSA framework utilized in conjunction with the invention assumes that the time signal is a linear combination of an orthonormal basis that is deduced from the correlation matrix of the time signal. Each envelope-detected time signal has a different orthonormal basis. The correlation matrix is diagonalized to allow for optimal denoising and easy detection of signal repetitions.

The present invention identifies seed-specific signal repetitions using eigenvalue pairs derived from a sliding window of envelope-detected backscattered rf echo signals processed using a correlation matrix. The correlation matrix, A, of the original time signal, s, is of size M by M, and element (i, j) is estimated by:

$$A_{i,j} = \frac{1}{N-M} \sum_{k=1}^{N-M} s(k)s(k+|i-j|), \quad (1)$$

where the time signal, s, is specifically the zero-mean envelope-detected backscattered rf signal, composed of N samples and having a sliding window of M(<N) samples. After computing and diagonalizing the correlation matrix, A, of the envelope signal, eigenvalues are ordered in decreasing order, $\lambda_1 > \ldots > \lambda_M$. The eigenvalues are real and positive because $A_{ij}$ is symmetric.

Each eigenvalue is equal to the variance of the signal in the corresponding Principal Component (PC) direction. Eigenvectors $E^1, \ldots, E^M$ are referred to as Empirical Orthonormal Functions (EOFs) and the projections of the original time signal, s, onto the EOF yields the principal components (PCs), $a^1, \ldots, a^M$. PCs $a^1, \ldots, a^M$, are obtained by projecting the envelope-detected time signal, s, over the empirical orthonormal functions (EOFs), also known as eigenvectors. Large eigenvalues are signal components while small eigenvalues are associated with noise. To get rid of noise, the time signal, s, is filtered by discarding all PCs corresponding to small eigenvalues. Eigenvalue, $\lambda_k$, is rejected where:

$$k > \text{Min}\left\{1, \text{ such that } \frac{\sum_{i=1}^{l} \lambda_i}{\sum_{i=1}^{M} \lambda_i} > 0.9\right\}. \quad (2)$$

Accordingly, all eigenvalues beyond 90% of the total variance of the signal (i.e., the sum of all eigenvalues:

$$\sum_{i=1}^{M} \lambda_i$$

are discarded. After rejecting noise-associated eigenvalues, only eigenvalues existing in pairs were retained.

After rejecting small eigenvalues, a second weeding process was conducted to remove unequal eigenvalues and spurious pairs. The second weeding process distinguished "actual" eigenvalue pairs, $\lambda_i$ and $\lambda_j$, from the remaining eigenvalues. As mentioned above, eigenvalue pairs are used to track repetitions as they are synonymous with signal periodicity. Non-noisy "actual" eigenvalue pairs were selected if all of the following conditions were true:

(1) i<k and j<k, where k is defined in Eq. (2);
(2) $|1-\lambda_i/\lambda_j|<0.04$; and
(3) The frequencies, $f_i$ and $f_j$, at which the spectra (i.e., the magnitude of the Fourier transform) of eigenvectors $E^i$ and $E^j$ reach their maxima, respectively, are such that $|1-f_i/f_j|<0.03$.

Condition (1) discards all eigenvalues assumed to be associated with noise, condition (2) allows for 4% tolerance to detect equal eigenvalues and condition (3) requires all eigenvalue pairs corresponding to repetitions to have EOFs with similar spectral content.

A new time signal (also known as the reconstructed signal), $s_r$, is constructed using the selected eigenvalue pairs, $\Gamma$, and summing the remaining PCs according to:

$$s_r(i+j) = \sum_{k \in \Gamma} a_i^k E_j^k \quad (3)$$

where the subscripts i and j represent the ith and jth components of the PC and EOF, respectively, and where:

$$a_i^k = \sum_{j=1}^{M} s_{i+j} E_j^k. \quad (4)$$

The Fourier transform, $S_r(f)$, of the new periodic signal, $s_r$, is then computed, and the spectral power, P, in the bandwidth of interest (i.e., that of the repetition frequency) is evaluated using:

$$P = \int_{f_0}^{f_1} |S_r(f)|^2 \, df. \quad (5)$$

P represents the power of the periodic part of the signal after optimal denoising in the frequency range close to that expected to be generated if a seed were present. Thus, P indicates the likelihood of the presence of a seed, but it does not disclose information on the location of the seed in the window. P is specific to the entire portion of the original signal, s, within the analysis window, thus the seed signal can be located anywhere in the analysis window.

As set forth above, the first part of a repetition signal can be shown experimentally to have a greater magnitude than the second part, leading to the determination that a seed is actually located at the first echo. Therefore, the location of the seed is considered to be where $s_r$ achieves its maximum amplitude.

Each backscattered signal is evaluated using SSA in a window size of N samples with an overlap percentage between adjacent windows. After the windowed signal is processed using the method of the present invention, a P value is obtained. This P value is added to the current P value at the location where $s_r$ achieves its maximum amplitude. The window is then shifted to the next location and the computation is repeated. After the SSA processing has been conducted over the entire A line, the algorithm moves to the next A line. Processing ends when all the lines are analyzed. The resulting P map is color-encoded in false color, and then superimposed on a B-mode image to form a P-mode image showing seed location. Higher values of P indicate a higher likelihood of the presence of a seed.

EXAMPLE

Figure 3A:
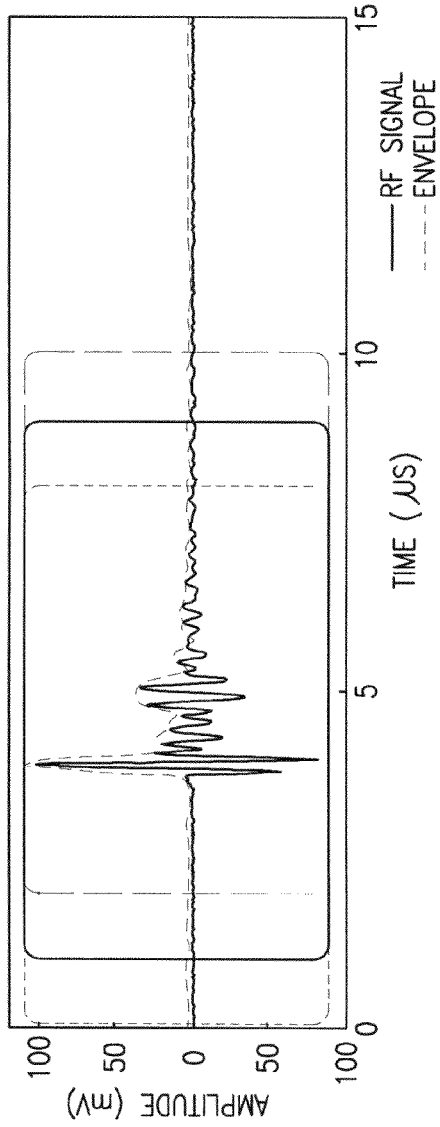
FIGS. 3A-3D show signals generated by the SSA method of the present invention.
Figure 3B:
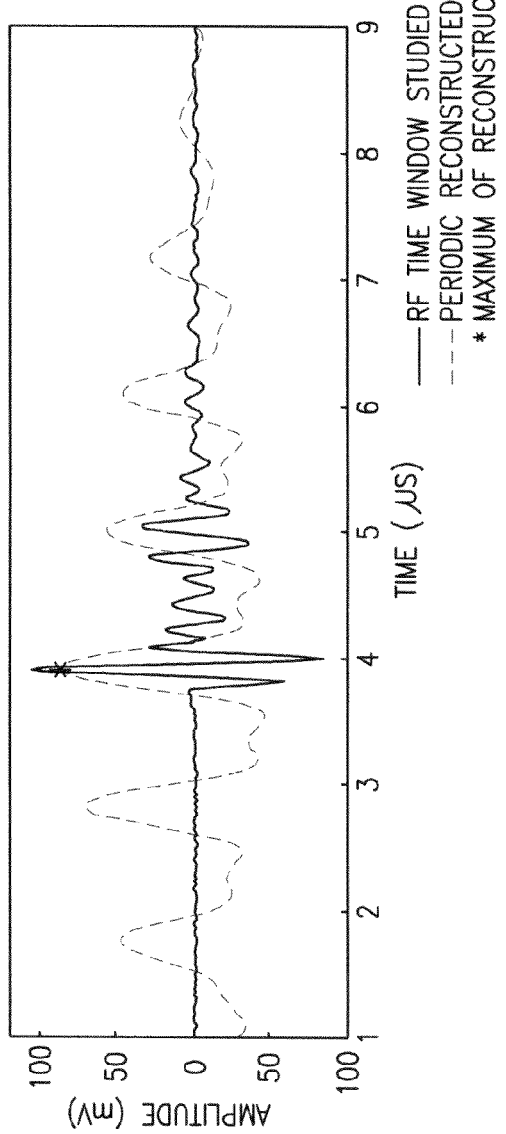

The method of the present invention can be illustrated by applying it to the center A line of the B-mode image of FIG. 1. The corresponding rf signal is shown in FIG. 2A. The first N samples were analyzed within the window indicated by the dashed rectangle in FIG. 3A; in this case, N is 400 and the sampling frequency was 50 MHz, so that 400 samples span 8 μs. M was chosen to be the half of N (i.e., 200 samples and 4 μs). The method is illustrated on the second 400-sample window with 87.5% overlap (i.e., spanning samples 51-450) as indicated by the bold rectangle in FIG. 3A. The 200-by-200 correlation matrix of this signal was estimated using Eq. (1), diagonalized, and eigenvalues were ordered from the largest to the smallest. Then, the cut-off eigenvalue is detected by finding the lowest value of index, k, such that Eq. (2) is true. For this example, k was 17. Among these 17 eigenvalues, two pairs of eigenvalues met the three requirements previously described. The reconstructed signal using these two pairs of eigenvalues is shown in FIG. 3B. The asterisk indicates where the reconstructed signal achieved its maximum amplitude.

Figure 3C:
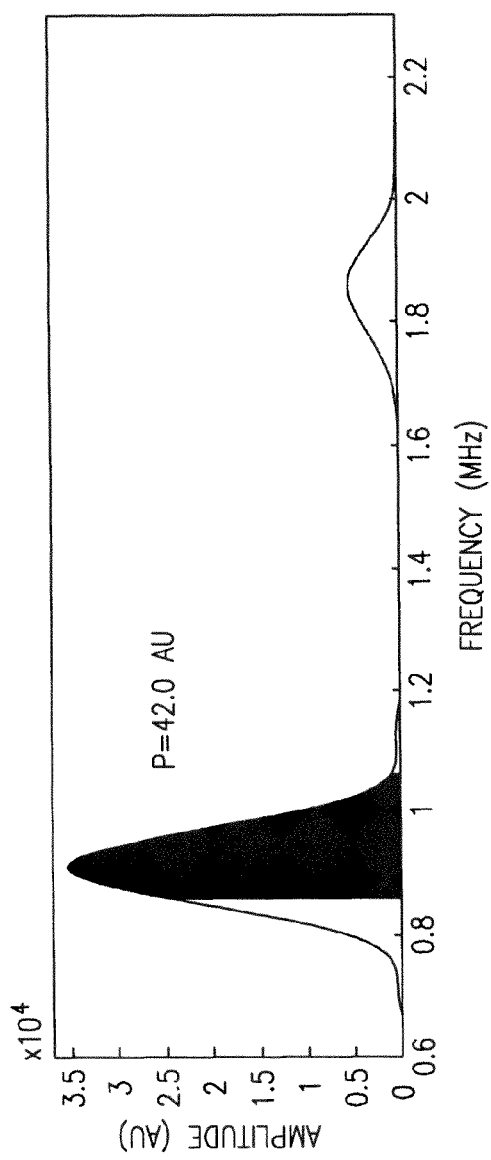

The spectrum (i.e., magnitude of the Fourier transform) of the reconstructed signal is shown in FIG. 3C. For this signal of a seed in a gel pad, the power integration of Eq. (5) was conducted over a frequency range of 0.86-1.06 MHz. This frequency range was chosen based on experimental observation of a repetition period of approximately 1.04 μs (which corresponds to a repetition frequency of 0.96 MHz) as illustrated by the location of the cepstral peak in FIG. 3C. The dark area under the curve in FIG. 3C depicts this integration, and the value of P for this segment was 42.0 in arbitrary units (AU). This value was added to the P plot at time sample 3.92 μs because it was the time sample at which $s_r$ reached its maximum, as denoted by an asterisk in FIG. 3B.

Figure 3D:
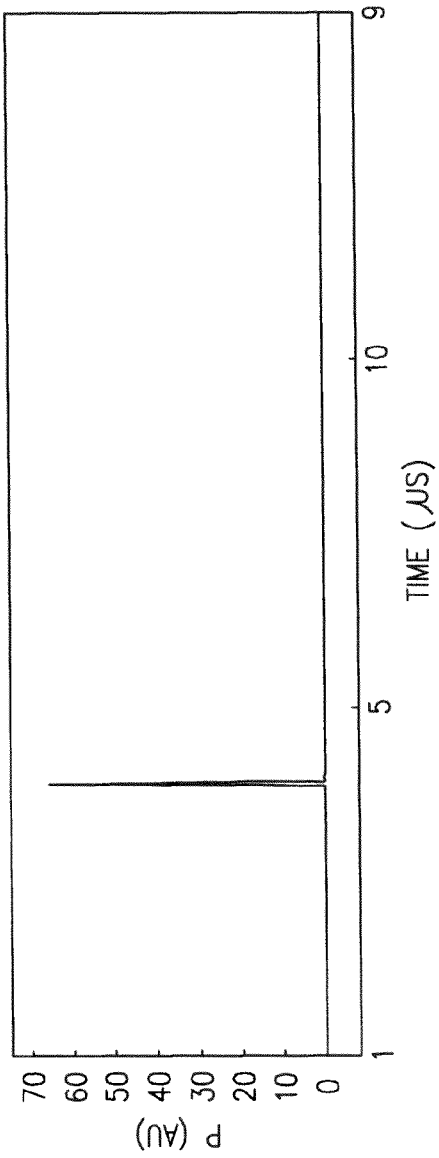

The algorithm utilized with the present invention continues by analyzing the next N-point window with 87.5% overlap (i.e. samples 101-500) and repeats itself until the entire signal is processed. The output of the algorithm is a P line, i.e. a signal with a length equal to the length of the original signal and with values indicating the relative likelihood of a seed being present. This P line is shown in FIG. 3D, which contains a very sharp peak near 3.94 μs. The amplitude of the peak is 65.5 AU which is greater than 42.0 AU because the other N-sample windows also contributed to the P value at this time point. Every A line was analyzed; the resulting P lines were merged together to form a two-dimensional matrix of P values. Then, the P values were normalized, log-compressed, color-encoded, and superimposed on the B-mode image to form the P-mode image.

Ex Vivo Example

In order to determine measurement accuracy, a seed was implanted in a piece of fresh, ex-vivo, degassed beef, and several planes were scanned with the 3.5 MHz transducer and processed using the inventive SSA method. In this setting, the true location of the seed was known because it was implanted into the piece of beef with a needle after the beef was degassed. This allowed for direct assessment of the method. Note that biological tissues are strong generators of speckle and also the small, spatial variations of acoustical properties that exist in tissue create scattering and phase aberrations. The experiment, described herein, was meant to evaluate the performance of the method in a challenging setting that is representative of conditions to be encountered in clinical applications.

Figure 4:
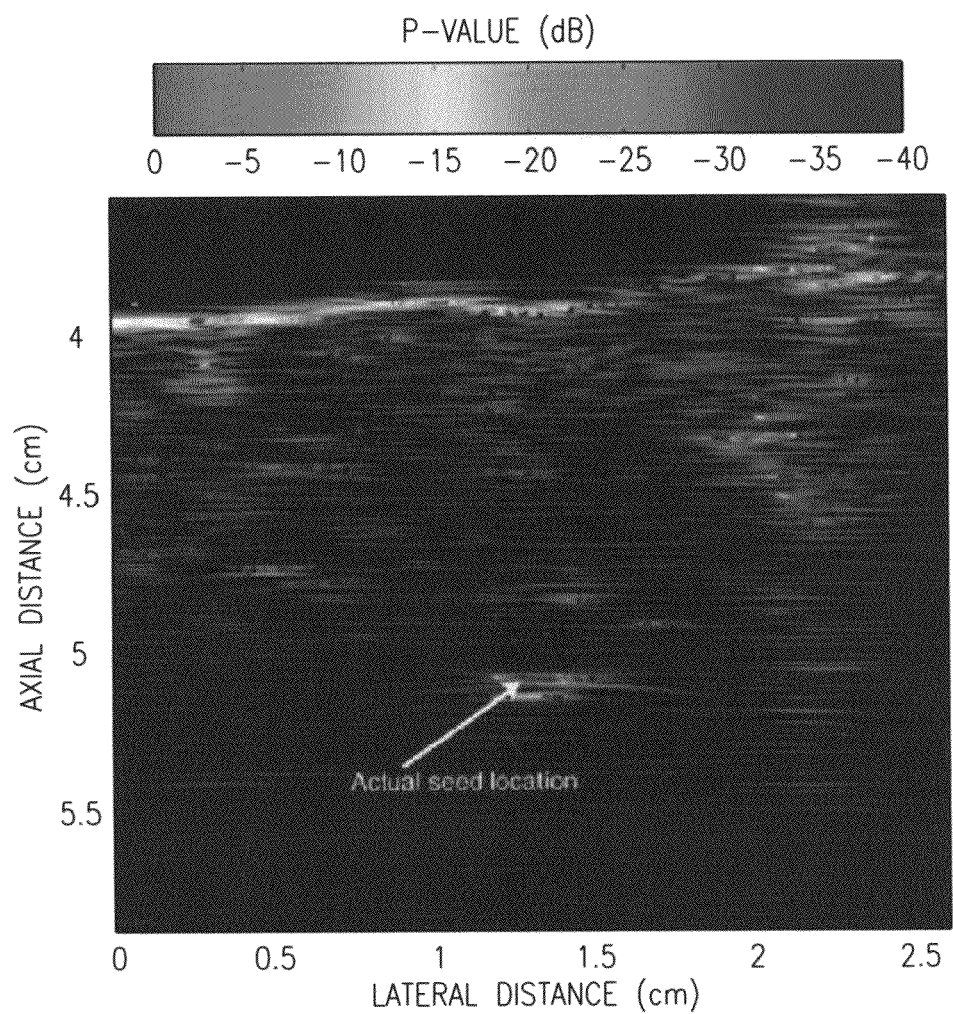
FIG. 4 shows a P-mode image.

FIG. 4 shows a P-mode image obtained ex vivo. The seed location is indicated by an arrow. The image shows that, for this case, P-value leakage clearly exists as indicated by the scattered light to dark blue squares present on the image. However, the leakage P-values remain low (<−30 dB); therefore, the leakage can be recognized clearly as noise. In FIG. 4, the largest P value is at the actual seed location, and, in this image, the seed is localized with high confidence using the inventive SSA method. In the same image, significant P values are scattered along the water-meat interface. In particular, a strong (about −3 dB) P value is displayed at an axial distance of approximately 3.7 cm and a lateral distance of 2.25 cm. In the absence of prior knowledge, this component could be interpreted as a seed, and if so, it would represent a false-positive interpretation. However, in the present case, prior knowledge of the water-meat boundary allows for easy dismissal of this potential false-positive assessment. The only other possible false-positive interpretation is located at an axial distance of 4.4 cm and a lateral distance of 2.1 cm. The P values at that location are about −10 dB, i.e., they are significantly lower than those of the actual seed.

In practice, a priori knowledge would be applied on a three-dimensional (3D) basis using adaptations of current clinical dosimetry-planning software to depict apparent seed locations in 3D. For example, if 40 seeds were implanted and 43 seeds were depicted, but 40 were shown to be within the gland and 3 were shown to be outside the gland, then a reasonable initial determination would be that all seeds were within the gland and their locations would be used to compute the actual dose distribution; a dose correction could be made by adding seeds if necessary. Similarly, if 40 seeds were implanted and 43 seeds were depicted, but only 37 were within the gland while 6 were shown to be outside it, then an inadequate dose to the gland would be established and a correction could be made immediately.

The present invention provides substantial advantages over prior art methods of seed localization and imaging because it allows seed detection and depiction to be performed independently of transducer technology or beam-forming algorithms. Furthermore, the method can be implemented readily in existing ultrasound instruments and its use would not require additional instrumentation, fixtures, or application techniques. These advantages provide for real-time clinical imaging of glands such as the prostrate.

The fact will be apparent to one of ordinary skill in the art that aspects of the invention, as described above, may be implemented in various forms of software, firmware and hardware. The actual software, firmware, or hardware used to practice the method of the present invention is not intended to be limiting to the breadth of the following claims. Those skilled in the art will recognize that other and further changes and modifications may be made to the embodiments described herein without departing from the spirit of the invention.

The invention claimed is:

1. A method for detecting brachytherapy seeds and determining their location in tissue, comprising:
   imaging a brachytherapy seed with an ultrasonic transducer to obtain radio-frequency (rf) echo signals;
   digitizing the rf echo signals and converting them to zero-mean envelope-detected signals, s;
   performing a singular spectrum analysis on the envelope-detected signals in a computing unit to obtain a periodic reconstructed signal $s_r$, wherein the analyzed envelope-detected signals are a time signal, s, composed of N samples, and that a sliding window of M samples is used to estimate a correlation matrix A where M N, wherein A is determined by:

$$A_{i,j} = \frac{1}{N-M} \sum_{k=1}^{N-M} s(k)s(k+|i-j|);$$

determining a P value indicative of the likelihood of seed presence based on the spectral power of $s_r$;
   determining a maximum amplitude of $s_r$; and
   using the maximum amplitude of $s_r$ to locate a brachytherapy seed in tissue.

2. The method in accordance with claim 1 further including diagonalization of A to obtain selected eigenvalues and ordering the eigenvalues from the largest to the smallest.

3. The method in accordance with claim 2 wherein certain eigenvalue pairs are selected from the ordered eigenvalues with the eigenvalue pairs being selected based upon predetermined heuristic criteria.

4. The method in accordance with claim 3 wherein a new time signal, $s_r$, is constructed from the selected eigenvalue pairs.

5. The method in accordance with claim 4 wherein $s_r$ is computed according to the following relationship:

$$s_r(i+j) = \sum_{k \in \Gamma} a_i^k E_j^k.$$

6. The method in accordance with claim 5 where the Fourier transform $S_r(f)$ of $s_r$ is computed.

7. The method in accordance with claim 6 wherein a spectral power, P, is computed based on $S_r(f)$ where the value of P is a number representing the relative likelihood of a seed being present in a particular location in the tissue.

* * * * *

UNITED STATES PATENT AND TRADEMARK OFFICE
CERTIFICATE OF CORRECTION

PATENT NO.        : 8,292,812 B2
APPLICATION NO.   : 12/004670
DATED             : October 23, 2012
INVENTOR(S)       : Ernest J. Feleppa et al.

It is certified that error appears in the above-identified patent and that said Letters Patent is hereby corrected as shown below:

In the Claims

Column 8; page 11; [Claim 1], lines 16 to 39, should be corrected as follows:

1. A method for detecting brachytherapy seeds and determining their location in tissue, comprising:

imaging a brachytherapy seed with an ultrasonic transducer to obtain radio-frequency *(rf)* echo signals;

digitizing the *rf* echo signals and converting them to zero-mean envelope-detected signals, $s$;

performing a singular spectrum analysis on the envelope-detected signals in a computing unit to obtain a periodic reconstructed signal $s_r$, wherein the analyzed envelope-detected signals are a time signal, $s$, composed of $N$ samples, and that a sliding window of $M$ samples is used to estimate a correlation matrix $A$ where $M < N$, wherein $A$ is determined by:

$$A_{i,j} = \frac{1}{N-M} \sum_{k=1}^{N-M} s(k)s(k+|i-j|)$$

determining a $P$ value indicative of the likelihood of seed presence based on the spectral power of $s_r$;

determining a maximum amplitude of $sr$: and using the maximum amplitude of $s_r$ to locate a brachytherapy seed in tissue.

Column 8; page 11; [Claim 7], lines 61 and 62, should be corrected as follows:

7. The method in accordance with claim 6 wherein a spectral power, $P$, is computed based on $S_r(f)$ where the value of $P$ is a number representing the relative likelihood of a seed being present in a particular location in the tissue.

Signed and Sealed this
Thirtieth Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,292,812 B2  
APPLICATION NO. : 12/004670  
DATED : October 23, 2012  
INVENTOR(S) : Ernest J. Feleppa et al.

It is certified that error appears in the above-identified patent and that said Letters Patent is hereby corrected as shown below:

In the Specification

Column 1, [Statement Regarding Federally Sponsored Research or Development], lines 8 and 9, first paragraph should be corrected as follows:

"This invention was made with government support under Grant CA098465 awarded by the National Institutes of Health. The government has certain rights in the invention."

Signed and Sealed this
Twelfth Day of November, 2013

Teresa Stanek Rea
*Deputy Director of the United States Patent and Trademark Office*